(12) United States Patent
Shyu

(10) Patent No.: US 6,856,916 B2
(45) Date of Patent: Feb. 15, 2005

(54) LOCATING SYSTEM OF OXIDATION/ REDUCTION POTENTIAL OF ELECTROLYSIS WATER AND THE CONSTANT OUTPUT METHOD OF CALIBRATION AND COMPENSATION THEREOF

(76) Inventor: Wen-Shing Shyu, 58, Ma Yuan West St., Taichung (TW)

(*) Notice: Subject to any disclaimer, the term of this patent is extended or adjusted under 35 U.S.C. 154(b) by 82 days.

(21) Appl. No.: 10/463,102

(22) Filed: Jun. 13, 2003

(65) Prior Publication Data

US 2004/0254744 A1 Dec. 16, 2004

(51) Int. Cl.⁷ .............................................. G01N 31/00
(52) U.S. Cl. ........................................................ 702/32
(58) Field of Search ................................ 702/22, 30–32, 702/64, 65, 85; 204/229.2, 229.3, 229.4, 229.5; 205/742–744

(56) References Cited

U.S. PATENT DOCUMENTS 6,251,259 B1 * 6/2001 Satoh et al. ................. 205/744

* cited by examiner

*Primary Examiner*—Michael Nghiem (57) ABSTRACT

A locating system of oxidation/reduction potential of the electrolysis water and the constant output method of calibration and compensation thereof are disclosed. Thus, the voltage of the electrolytic bath can be regulated so as to control an electrolytic current of the electrolytic bath exactly, so that the electrolytic current of the electrolytic bath is maintained at a constant value.

14 Claims, 10 Drawing Sheets

LOCATING SYSTEM OF OXIDATION/REDUCTION POTENTIAL OF ELECTROLYSIS WATER AND THE CONSTANT OUTPUT METHOD OF CALIBRATION AND COMPENSATION THEREOF

BACKGROUND OF THE INVENTION

1. Field of the Invention

The present invention primarily relates to a locating system of oxidation/reduction potential of the electrolysis water and the constant output method of calibration and compensation thereof.

2. Description of the Related Art

Usually, in testing the alkaline reduction water produced by the electrolysis water, for example, the drinking water, when the reduction potential is ranged between −200 mv and −400 mv, the alkaline reduction water has a better anti-oxidation effect. For the industrial washing equipment, when the reduction potential is ranged between −800 mv and −1,000 mv, the alkaline reduction water has a better anti-oxidation and rustproof effect. On the other hand, when the oxidation potential is about +750 mv, the weak acid oxidation water is available for cosmetics, and when the oxidation potential is ranged between +960 mv and +1,200 mv, the strong acid oxidation water is available for sterilization.

The generator of the electrolysis water in the market can be used to passively test the oxidation/reduction potential of the electrolysis water by the testing instruments during a constant time interval. However, the generator of the electrolysis water cannot be used to automatically detect, indicate and compensate the oxidation/reduction potential of the electrolysis water, so that the user cannot immediately know if the oxidation/reduction potential of the daily used electrolysis water satisfies the standard. In addition, the impurities or the deposited calcium contained in the water easily block the sensor mounted in the testing instruments, thereby causing errors in the measured results.

SUMMARY OF THE INVENTION

The objective of the present invention is to solve the following problem in that, when the water is electrolyzed, the wall of the cathode tube will absorb the positive ion (such as the calcium ion), so that the calcium is deposited on the wall of the cathode tube during a period of time, thereby increasing the impedance in the electrolytic bath during the electrolysis action, and thereby decreasing the current density, such that the oxidation/reduction potential of the electrolysis water is decreased gradually to approach the original potential.

Accordingly, the objective of the present invention is to provide a locating system of oxidation/reduction potential of the electrolysis water and the constant output method of calibration and compensation thereof, so as to solve the above-mentioned problem.

According to the first objective of the present invention, the water flow controller can control the flow speed of input water to obtain a constant electrolytic time.

According to the second objective of the present invention, the PH value detector detects the PH value in the water and the TDS test detects the total solid quantity in the water. Then, the data are sent into the CPU which compares the oxidation/reduction potential indicated by the liquid crystal display with the oxidation/reduction potential of the actual electrolysis water, so as to calibrate the upper and lower limits.

According to the third objective of the present invention, the ideal section of the oxidation/reduction potential is selected according to the oxidation/reduction potential indicated by the liquid crystal display to perform a step control according to the relative electrolysis current of the ideal section to obtain the step selection of the oxidation/reduction potential.

According to the fourth objective of the present invention, the user can select the ideal section according to the oxidation/reduction potential indicated by the liquid crystal display, and the circuit control system can regulate the voltage according to the relative current of the ideal section to keep the current at a constant so as to maintain the oxidation/reduction potential at the ideal section.

According to the fifth objective of the present invention, when the resistance in the electrolytic bath is increased to the upper limit and the regulated voltage is also increased to the upper limit, the liquid crystal display can indicate the critical oxidation/reduction potential to remind the user of cleaning the electrolytic bath to decrease the resistance in the electrolytic bath.

In accordance with the present invention, there is provided a constant output method of calibration and compensation of a locating system of oxidation/reduction potential of an electrolysis water, comprising the steps of:

storing experimental data, coordinate parameters and expressions of an oxidation/reduction potential relative to a plurality of primary factors in a central processing unit to obtain indication values;

detecting actual data of the oxidation/reduction potential of an actual electrolysis water;

comparing and calibrating the indication values with the oxidation/reduction potential of the actual electrolysis water;

selecting an ideal section of the oxidation/reduction potential according to the actual indication values;

performing a step control according to a relative electrolytic current of the ideal section to select the step of the oxidation/reduction potential;

detecting changes of resistance of an electrolytic bath; and regulating a voltage of the electrolytic bath so as to control an electrolytic current of the electrolytic bath exactly, so that the electrolytic current of the electrolytic bath is maintained at a constant value.

Further benefits and advantages of the present invention will become apparent after a careful reading of the detailed description with appropriate reference to the accompanying drawings.

DETAILED DESCRIPTION OF THE INVENTION

According to the results of experiments, it is found that, when the electrolytic bath has a fixed structure (such as the material of electrode, the kinds of diaphragm, the relative area and distance between the positive pole and the negative pole), the primary factors affecting the oxidation/reduction potential of the electrolysis water include:

1. The electrolytic time (the flow speed of input water);
2. The electrolytic current (the current density); and
3. The kinds of electrolyte (the proportion and concentration of negative and positive ions).

Figure 1:
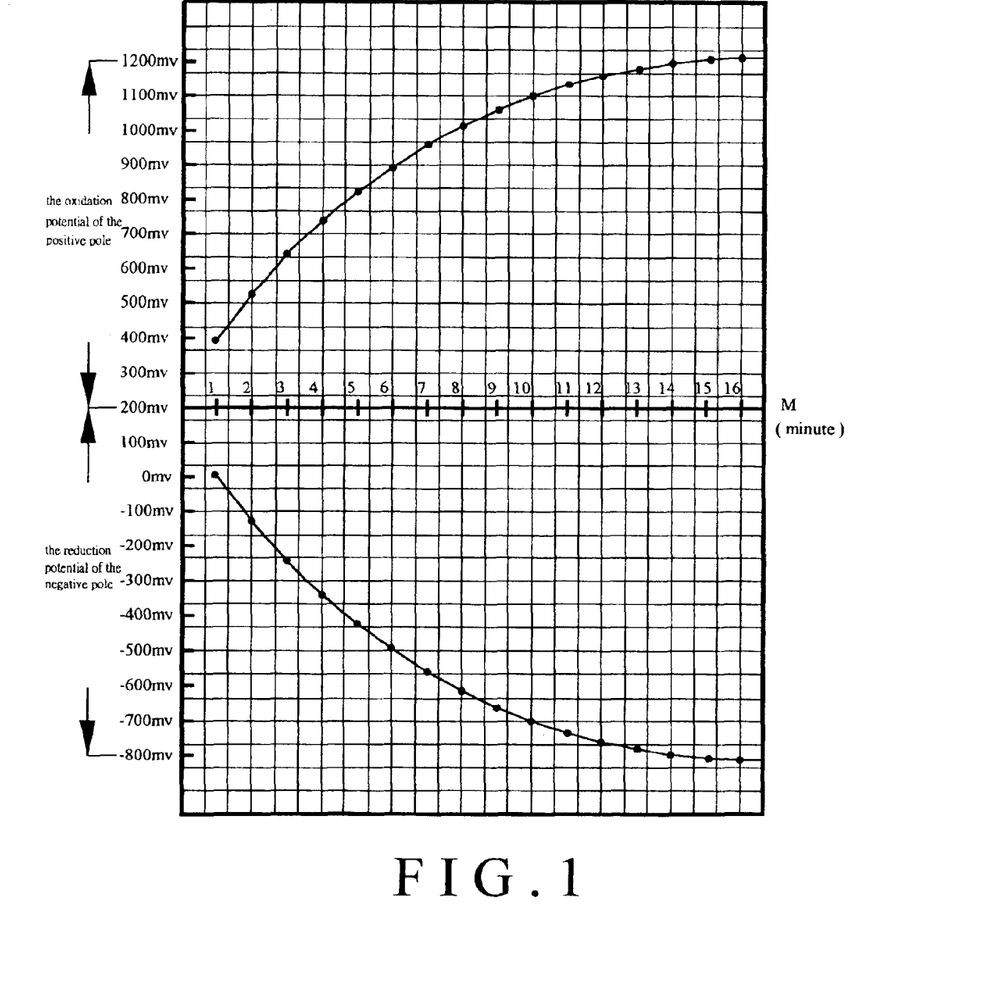
FIG. 1 is a coordinate graph of the experimental data of the electrolytic time versus the oxidation/reduction potential of the electrolysis water in accordance with the present invention.
Figure 2:
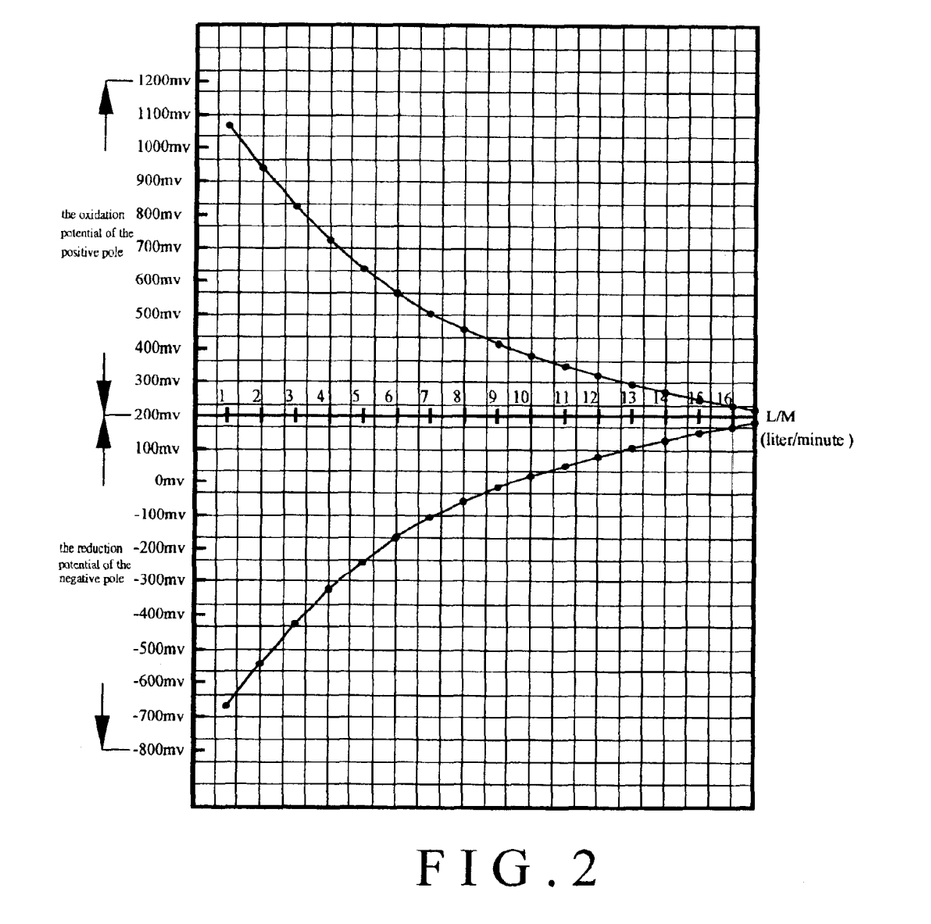
FIG. 2 is a coordinate graph of the experimental data of the flow speed of input water versus the oxidation/reduction potential of the electrolysis water in accordance with the present invention.

Referring to the drawings and initially to FIGS. 1 and 2, FIG. 1 is a coordinate graph of experimental data of the electrolytic time versus the oxidation/reduction potential of the electrolysis water, and FIG. 2 is a coordinate graph of experimental data of the flow speed of input water versus the oxidation/reduction potential of the electrolysis water. In such a manner, the flow speed of input water is decreased when the electrolytic time is increased. As shown in FIG. 1, when the electrolytic time is increased, the oxidation potential of the oxidation water obtained by the positive pole is increased gradually. For example, the oxidation potential of the oxidation water is indicated by positive values, and is increased from +200 mv to +1200 mv. In addition, when the electrolytic time is increased, the reduction potential of the reduction water obtained by the negative pole is decreased gradually. For example, the reduction potential of the reduction water is indicated by negative values, and is decreased from −200 mv to −800 mv. Thus, when the oxidation potential of the oxidation water is increased, the oxidation water has a stronger oxidation capacity, and when the reduction potential of the reduction water is decreased, the reduction water has a stronger reduction capacity.

Figure 3:
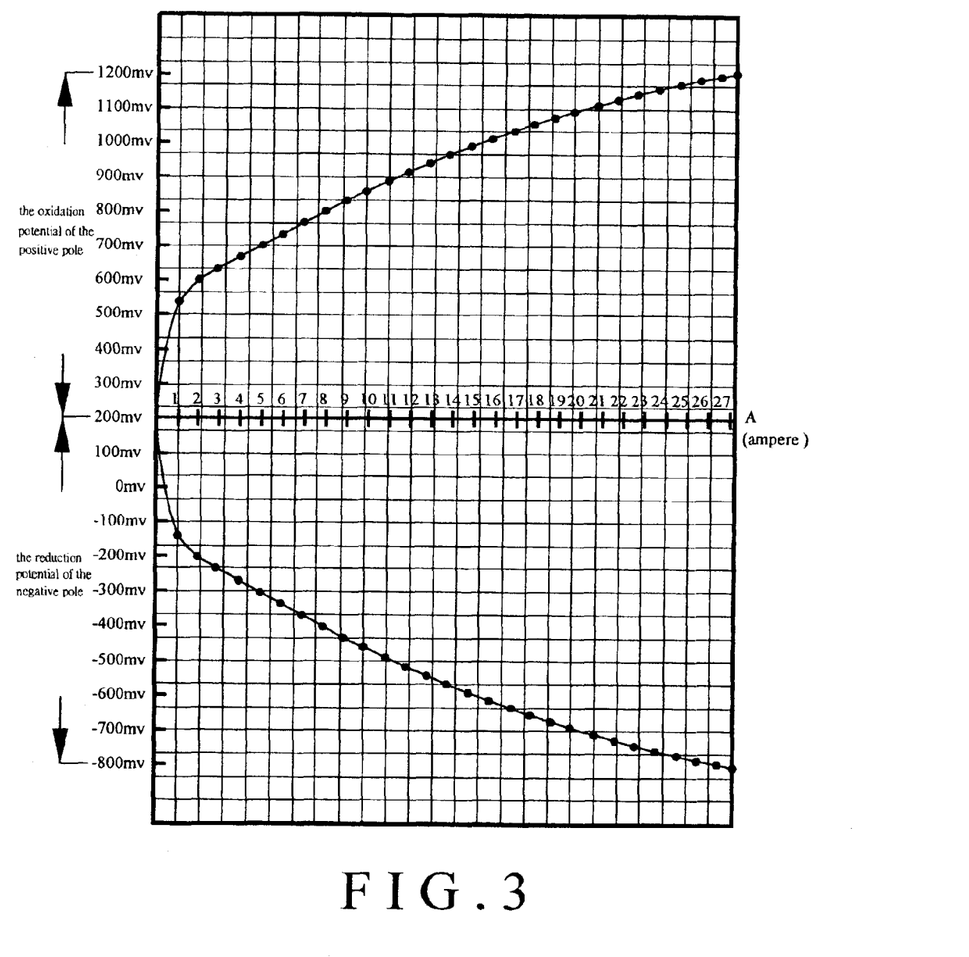
FIG. 3 is a coordinate graph of the experimental data of the electrolytic current versus the oxidation/reduction potential of the electrolysis water in accordance with the present invention.

Referring to FIG. 3, FIG. 3 is a coordinate graph of experimental data of the electrolytic current versus the oxidation/reduction potential. In such a manner, when the electrolytic current (the current density) is increased, the oxidation potential of the oxidation water obtained by the positive pole is increased gradually. For example, the oxidation potential of the oxidation water is indicated by positive values, and is increased from +200 mv to +1200 mv. In addition, when the electrolytic current is increased, the reduction potential of the reduction water obtained by the negative pole is decreased gradually. For example, the reduction potential of the reduction water is indicated by negative values, and is decreased from −200 mv to −800 mv. Thus, when the oxidation potential of the oxidation water is increased, the oxidation water has a stronger oxidation capacity, and when the reduction potential of the reduction water is decreased, the reduction water has a stronger reduction capacity.

Figure 4:
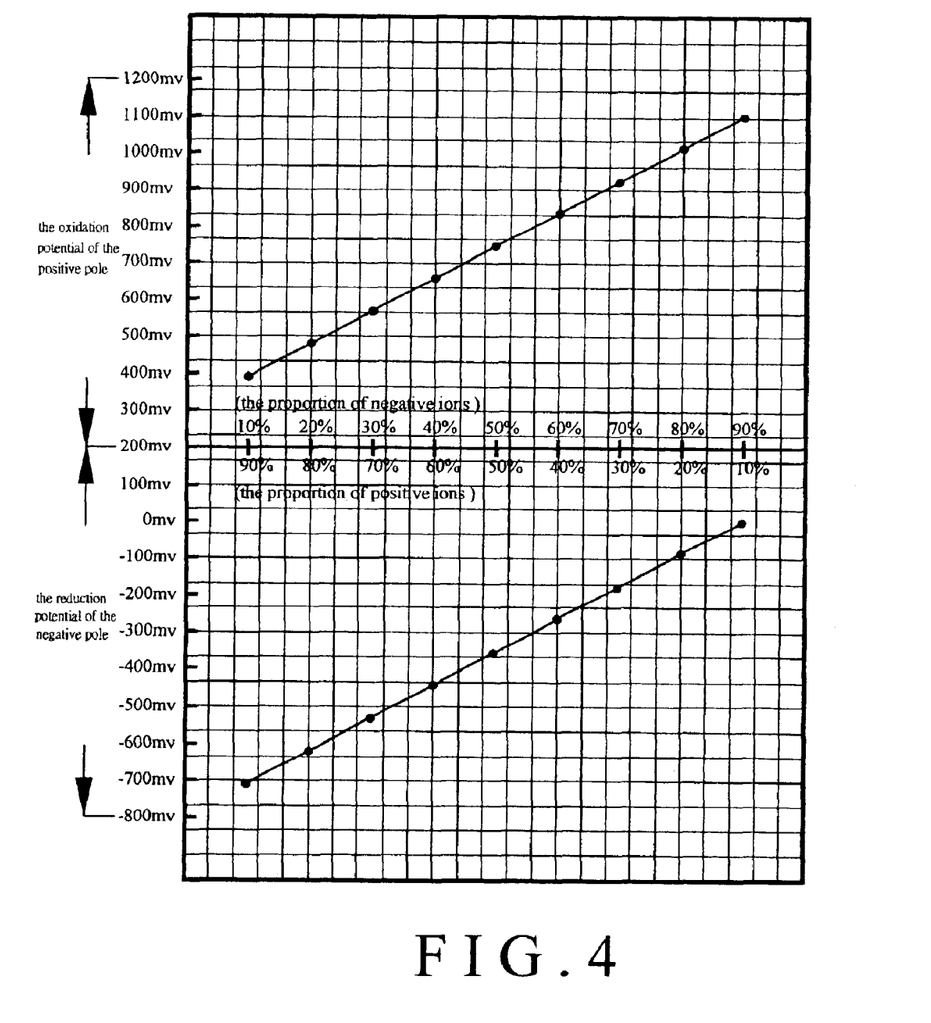
FIG. 4 is a coordinate graph of the experimental data of the proportion of negative and positive ions (the kinds of electrolyte) versus the oxidation/reduction potential of the electrolysis water in accordance with the present invention.

Referring to FIG. 4, FIG. 4 is the coordinate graph of the experimental data of the proportion of negative and positive ions (the kinds of electrolyte) versus the oxidation/reduction potential of the electrolysis water. In such a manner, when the proportion of positive ions (such as calcium, magnesium, sodium, potassium, etc.) contained in the electrolyte is increased, the reduction potential of the reduction water obtained by the negative pole is decreased gradually. Thus, when the reduction potential of the reduction water is decreased, the reduction water has a stronger reduction capacity. In addition, when the proportion of negative ions (such as oxalic, carbonic acid, phosphoric acid, etc.) contained in the electrolyte is increased, the oxidation potential of the oxidation water obtained by the positive pole is increased gradually. Thus, when the oxidation potential of the oxidation water is increased, the oxidation water has a stronger oxidation capacity.

Figure 5:
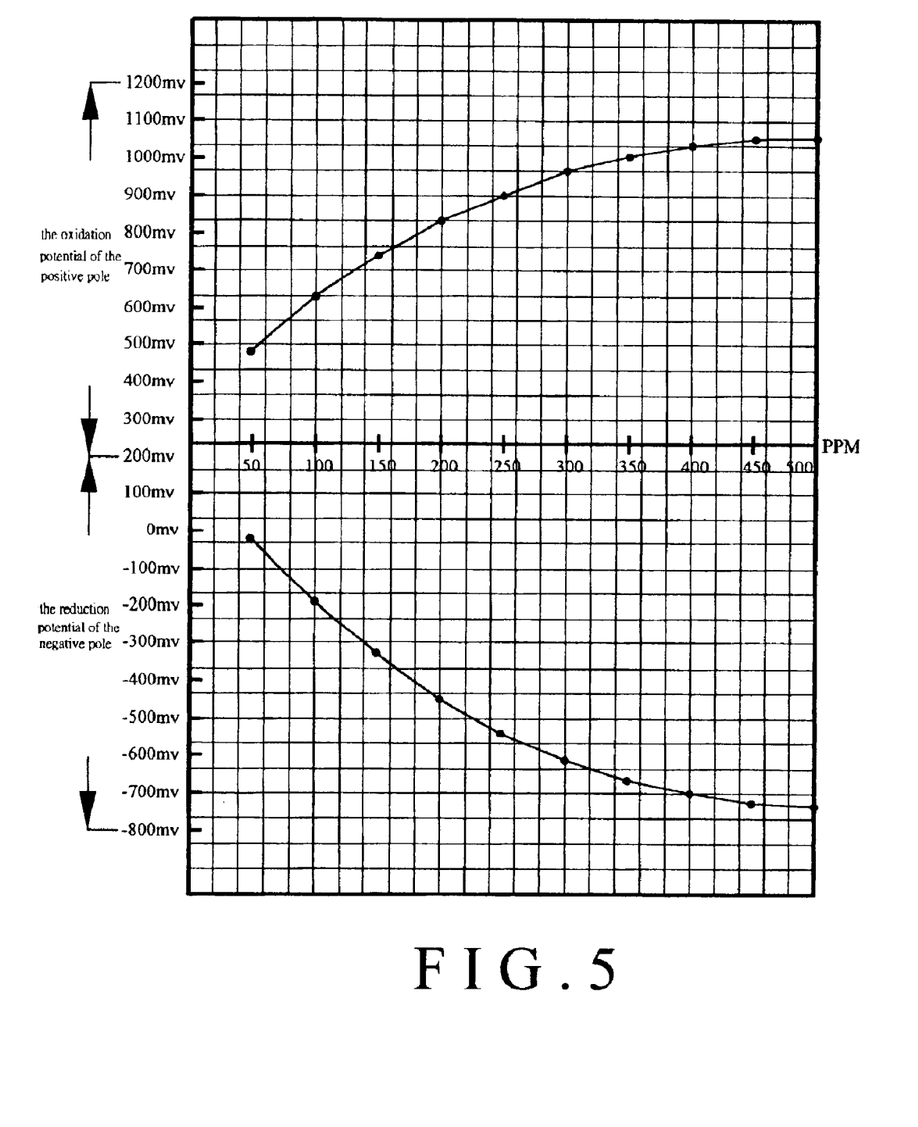
FIG. 5 is a coordinate graph of the experimental data of the concentration of negative and positive ions (the kinds of electrolyte) versus the oxidation/reduction potential of the electrolysis water in accordance with the present invention.

Referring to FIG. 5, FIG. 5 is the coordinate graph of the experimental data of the concentration of negative and positive ions (the kinds of electrolyte) versus the oxidation/reduction potential of the electrolysis water. In such a manner, when the concentration of negative and positive ions contained in the electrolyte is increased, the reduction potential of the reduction water obtained by the negative pole is decreased gradually. Thus, when the reduction potential of the reduction water is decreased, the reduction water has a stronger reduction capacity. In addition, when the concentration of negative and positive ions contained in the electrolyte is increased, the oxidation potential of the oxidation water obtained by the positive pole is increased gradually. Thus, when the oxidation potential of the oxidation water is increased, the oxidation water has a stronger oxidation capacity.

According to the electrolytic time (the flow speed of input water), the electrolytic current (the current density) and the kinds of electrolyte (the proportion and concentration of negative and positive ions), the related experimental data can be used to make the coordinate parameters as follows:

1. The electrolytic time (the flow speed of input water) is 4 liters per minute;
2. The proportion of negative and positive ions:
   the proportion of negative ions is 50%;
   the proportion of positive ions is 50%; and
3. The concentration of negative and positive ions:
   the concentration of negative and positive ions is 150 ppm.

Figure 6:
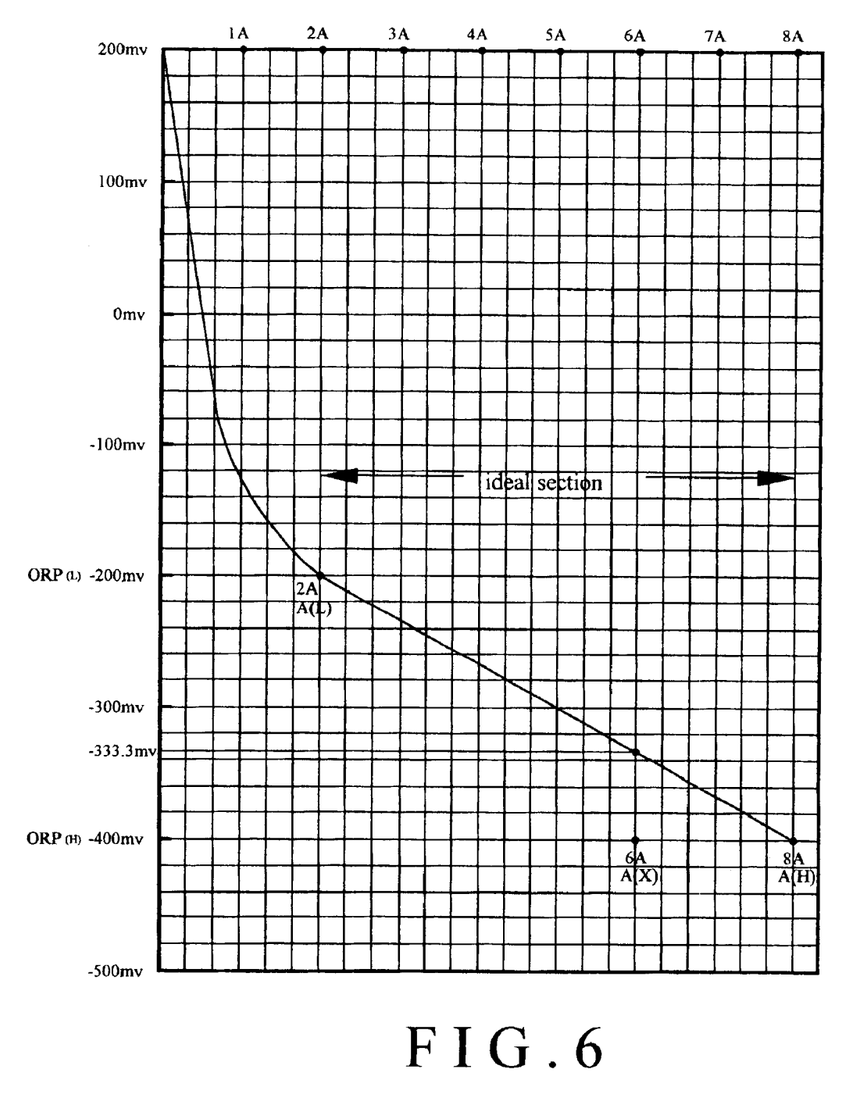
FIG. 6 is a coordinate graph of the experimental data of the electrolytic current versus the oxidation/reduction potential of the electrolysis water in accordance with the present invention, wherein the electrolytic time and the kinds of electrolyte are constant.

Referring to FIG. 6, FIG. 6 is a coordinate graph of the experimental data of the electrolytic current versus the oxidation/reduction potential of the electrolysis water, wherein the electrolytic time and the kinds of electrolyte are constant. According to a relationship between the magnitude of the electrolytic current and the values of the oxidation/reduction potential (ORP), the ideal section of the oxidation/reduction potential is decided as follows. For example, the oxidation potential of the oxidation water is ranged between +960 mv and +1200 mv, and the reduction potential of the reduction water is ranged between −200 mv and −400 mv.

Thus, according to the electrolytic current of the ideal section, the step control is determined as follow. If the electrolytic current of the ideal section is from 2 A to 8 A, the electrolytic current of the ideal section can be divided into five steps or multiple steps from 2 A to 8 A, thereby obtaining the step selection of the oxidation/reduction potential of the electrolysis water as follows:

ORP (indication value) =
ORP(L) + [A(X) − A(L)]*[ORP(H) − ORP(L)]/[A(H) − A(L)], wherein:

ORP (indication value) is the actual indication value of the liquid crystal display (LCD);
ORP(L) is the measured value of the first-step oxidation/reduction potential;
ORP(H) is the measured value of the last-step oxidation/reduction potential;
A(L) is the measured first-step minimum current value;
A(H) is the measured last-step minimum current value; and
A(X) is the selected current value of the actual section.

For example, when ORP(H)=−400 mv, the electrolytic current is 8 A (that is, A(H)=8 A), and when ORP(L)=−200 mv, the electrolytic current is 2 A (that is, A(L)=2 A).

If the third-step is selected, A(X)=6 A.

Thus, ORP (indication value) =
ORP(L) + [A(X) − A(L)]*[ORP(H) − ORP(L)]/[A(H) − A(L)] =
−200 mv + (6A − 2A)*[(−400 mv) − (−200 mv)]/[8A − 2A] =
−200 mv + 4A*(−200 mv)/6A =
−200 mv + 4A*(−33.3 mv/A) =
−200 mv + (−133.2 mv) =
−333.2 mv.

Thus, the oxidation/reduction potential is equal to −333.2 mv.

Then, the above-mentioned experimental data and expressions are stored in the data base of the central processing unit (CPU). By using the detection member (the flow meter), the shunt resistance detection circuit, the TDS test (measuring the total solid quantity), the PH value test, the central processing unit can calculate and compare the results. Then, the central processing unit can compare the oxidation/reduction potential value indicated by the liquid crystal display with the oxidation/reduction potential value of the actual electrolysis water, and can calibrate the upper and lower limits.

Figure 7:
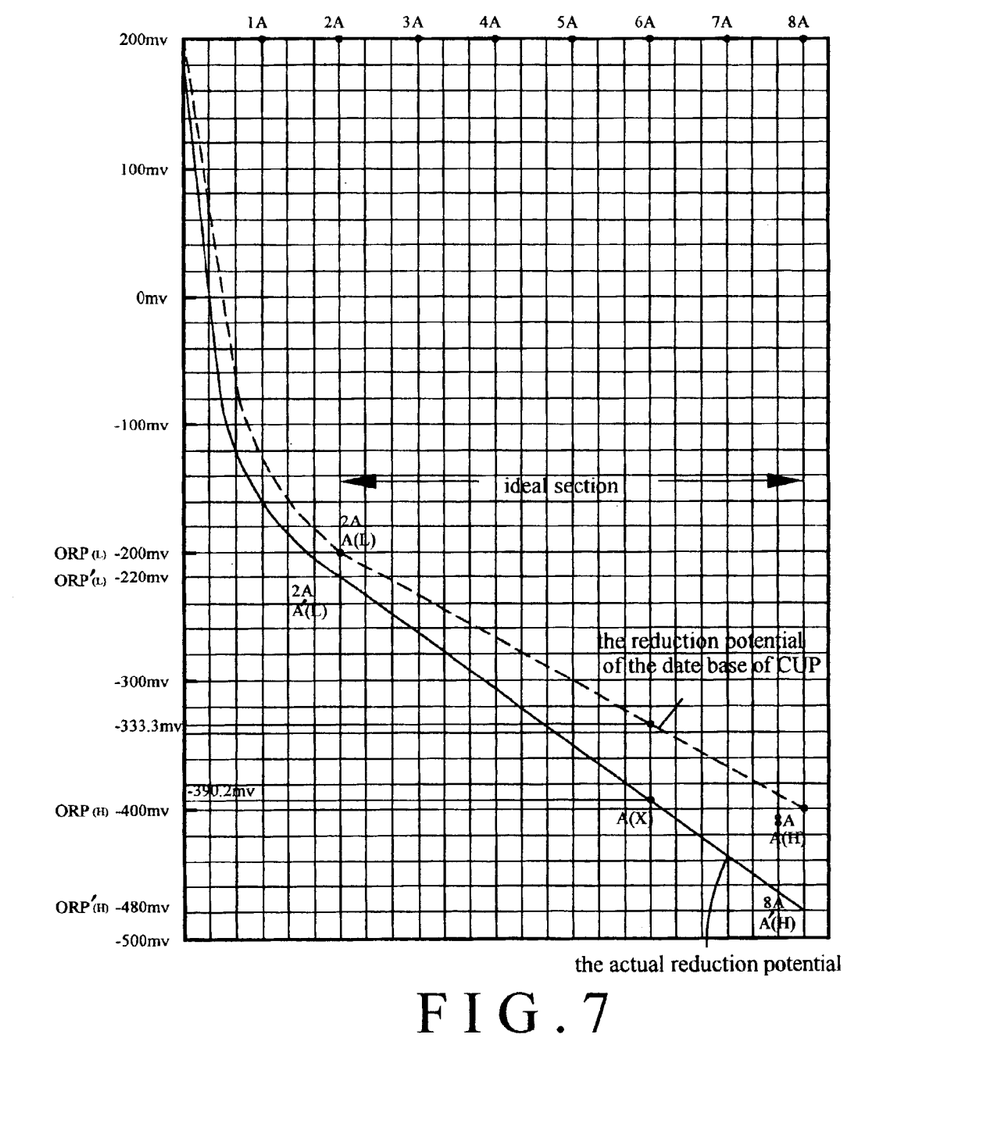
FIG. 7 is a coordinate graph of the experimental data of calibration of the upper and lower limits of the oxidation/reduction potential of the actual electrolysis water in accordance with the present invention.

Referring to FIG. 7, FIG. 7 is a coordinate graph of the experimental data of calibration of the upper and lower limits of the oxidation/reduction potential of the actual electrolysis water.

The expression of the oxidation/reduction potential is as follows.

ORP (indication value) =
ORP'(L) + [A'(X) − A'(L)]*[ORP'(H) − ORP'(L)]/[A'(H) − A'(L)], wherein:
ORP (indication value) is the actual indication value of the liquid crystal display (LCD);
ORP'(L) is the measured value of the first-step oxidation/reduction potential and is equal to −220 mv;
ORP'(H) is the measured value of the last-step oxidation/reduction potential and is equal to −480 mv;
A'(L) is the measured first-step minimum current value and is equal to 2 A;
A'(H) is the measured last-step minimum current value and is equal to 8 A; and
A'(X) is the selected current value of the actual section (the third step is selected) and is equal to 6 A.

Thus, ORP (indication value) =
ORP'(L) + [A'(X) − A'(L)]*[ORP'(H) − ORP'(L)]/[A'(H) − A'(L)] =
−220 mv + (6A − 2A)*[(−480 mv) − (−200 mv)]/[8A − 2A] =
−220 mv + 4A*(−260 mv)/6A =
−220 mv + 4A*(−43.3 mv/A) =
−220 mv + (−173.2 mv) =
−393.2 mv.

Thus, the oxidation/reduction potential is equal to −393.2 mv.

At this time, the liquid crystal display indicates the relationship between the electrolytic current and the oxidation/reduction potential value of the electrolysis water. Then, according to the indicated oxidation/reduction potential value, the ideal section of the electrolytic current or the relative oxidation/reduction potential value is selected. After the relative electrolytic current of the oxidation/reduction potential of the selected section is set, the detection circuit can detect variation of the resistance in the electrolysis bath. Then, by the depression of V (voltage)=I (current)*R (resistance), the electrolytic current can be maintained at a constant by adjusting the working voltage relative to the resistance. Thus, when the resistance in the electrolysis bath is increased, the working voltage is increased, so that the electrolytic current can be maintained at a constant, so as to exactly control the electrolytic current in the electrolysis water according to the selected section.

Figure 8:
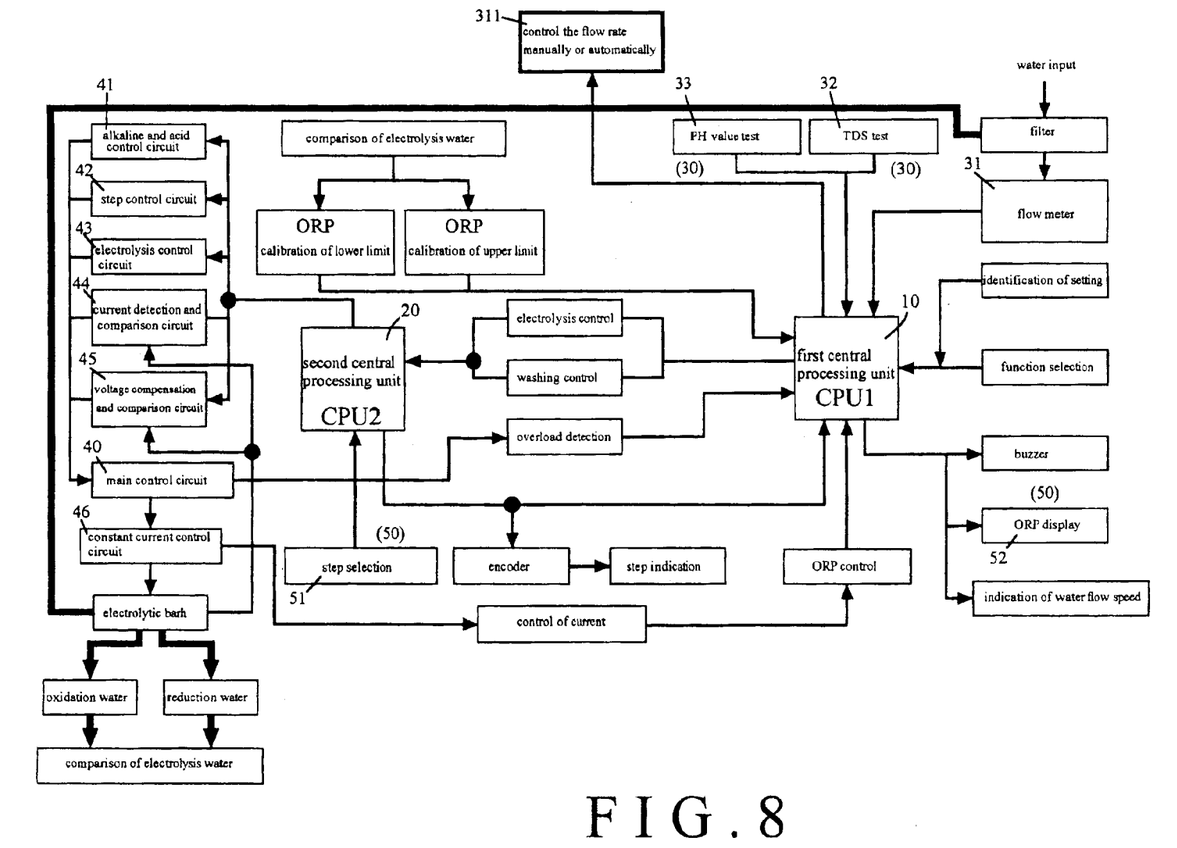
FIG. 8 is a block diagram of a locating system of oxidation/reduction potential of the electrolysis water in accordance with the present invention.

Referring to FIG. 8, the locating system of oxidation/reduction potential of the electrolysis water in accordance with the present invention comprises a first central processing unit (CPU1) 10, a second central processing unit (CPU2) 20, a detection member 30, a main control circuit 40, and a manipulation unit 50.

The first central processing unit 10 can receive the experimental data as shown in FIGS. 1–7, such as the electrolytic time, the flow speed of input water, the electrolytic current (the current density), the kinds of electrolyte (the proportion and concentration of negative and positive ions), and the related expressions. In addition, the first central processing unit 10 includes functions of calculation, comparison, and input and output of signals.

The expression of the oxidation/reduction potential is as follows:

ORP (indication value) =
ORP(L) + [A(X) − A(L)]*[ORP(H) − ORP(L)]/[A(H) − A(L)], wherein:

The second central processing unit 20 is used to control operation of the main control circuit 40.

The detection member 30 includes a flow meter 31, a TDS test 32 (measuring the total solid quantity), a PH value test 33, and a shunt resistor 34.

The flow meter 31 is used to detect the flow speed of input water in the electrolytic bath, and to transmit the signals to the data base of the first central processing unit 10 to manually or automatically control the flow rate 311, so as to control the electrolytic time and the flow speed of input water.

The TDS test 32 is used to detect the total solid quantity of negative and positive ions in the water before electrolysis, and to transmit the signals to the data base of the first central processing unit 10 to function as the basis of the oxidation/reduction potential in the water.

The PH value test 33 is used to detect the PH value in the water before electrolysis, and to transmit the signals to the data base of the first central processing unit 10 to function as the basis of the oxidation/reduction potential in the water.

The ORP test equipment can detect the oxidation/reduction potential of the electrolysis water, and to transmit the signals to the data base of the first central processing unit 10 for calibration of the upper and lower limits.

Figure 9:
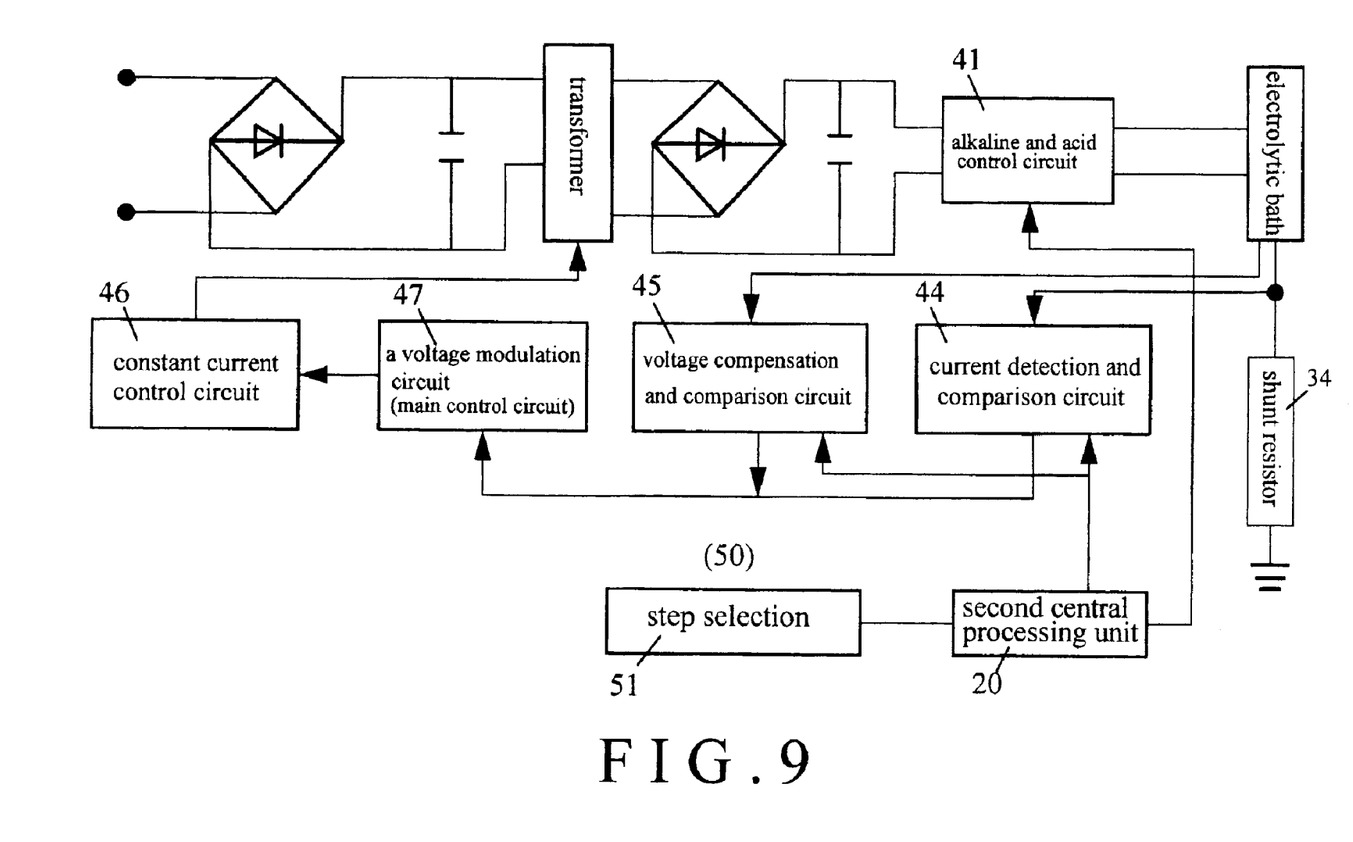
FIG. 9 is a circuit diagram of a locating system of oxidation/reduction potential of the electrolysis water in accordance with the present invention.

Referring to FIG. 9, the main control circuit 40 includes an alkaline and acid control circuit 41, a step control circuit 42, an electrolysis control circuit 43, a current detection and comparison circuit 44, a voltage compensation and comparison circuit 45, a constant current control circuit 46 (having a gate driver), and a voltage modulation circuit 47.

The electrolytic bath is provided with a shunt resistor 34. The current detection and comparison circuit 44 and the voltage compensation and comparison circuit 45 can drive the voltage modulation circuit 47 and the gate driver of the constant current control circuit 46 to regulate the voltage, so that the output current is kept constant.

Figure 10:
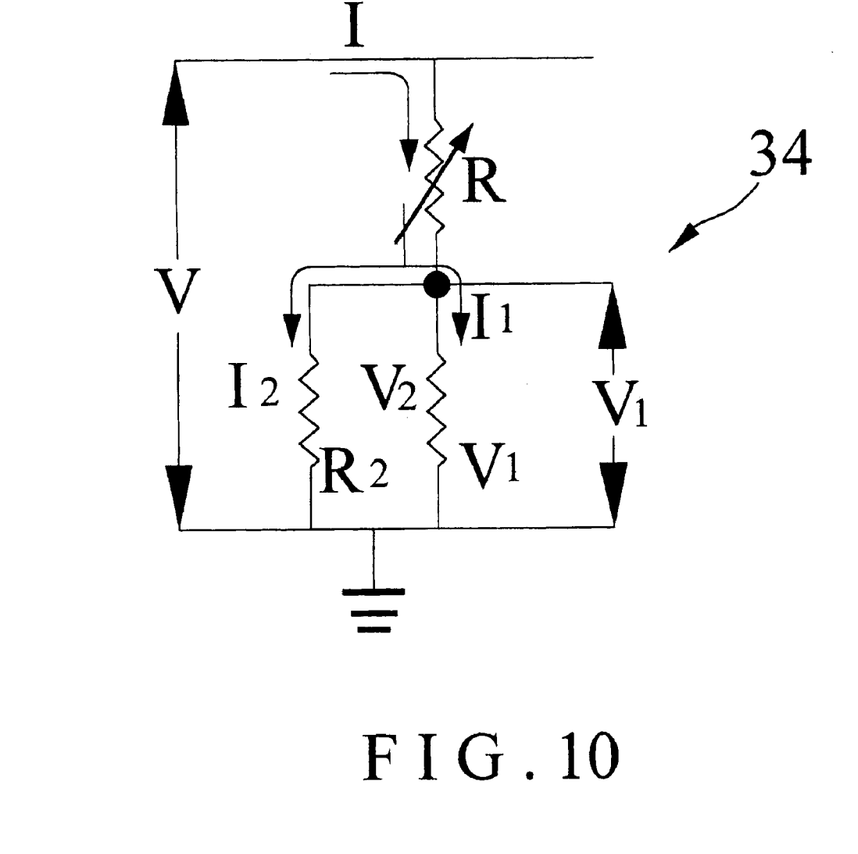
FIG. 10 is a circuit diagram of a shunt resistor of the locating system of oxidation/reduction potential of the electrolysis water in accordance with the present invention.

Referring to FIG. 10, the circuit of the shunt resistor 34 is shown, wherein:

V is the working voltage of the actual electrolysis;

I is the total current passing through the electrolytic bath;

R is the actual resistance of the electrolytic bath (variable resistance, for example, when the calcium is deposited in the electrolytic bath, the resistance is increased); and $R_1$ and $R_2$ are the shunt resistance serially connected in the electrolytic bath.

In such a manner, $I=I_1+I_2$ and $V_1=I_1*R_1=V_2=I_2*R_2$.

Thus, when the actual resistance R is increased (the resistance in the electrolytic bath is increased), the total current I is decreased (the electrolytic current is decreased), so that the currents $I_1$ and $I_2$ of the shunt resistance $R_1$ and $R_2$ are decreased. Each of the shunt resistance $R_1$ and $R_2$ is fixed, so that when the total current I is decreased, the working voltage V is also decreased. By the expression of $V_1=I_1*R_1=V_2=I_2*R_2$, the change of the total current I can be detected by the change of $V_1$.

At this time, the current detection and comparison circuit 44 and the voltage compensation and comparison circuit 45 can drive the voltage modulation circuit 47 and the gate driver of the constant current control circuit 46 to regulate the working voltage V of the actual electrolysis.

Each of the shunt resistance $R_1$ and $R_2$ is fixed, so that the currents $I_1$ and $I_2$ can be kept constant, and the voltage $V_1$ can also be kept constant. By the expression of $I=I_1+I_2$, when the currents $I_1$ and $I_2$ is kept constant, the total current I is also kept constant. Thus, the output of the total current I can be kept constant.

The voltage modulation circuit 47 of the main control circuit 40 is an interchangeable transform or a frequency oscillation modulation circuit. The voltage modulation circuit 47 of the main control circuit 40 is controlled by the second central processing unit 20 to increase or decrease the voltage so as to increase or decrease the current, so that the total current can be kept constant.

The manipulation unit 50 at least includes a step selection 51 and an ORP display 52. Thus, the manipulation unit 50 can preset and calibrate the oxidation/reduction potential value indicated by the liquid crystal display according to the proportion and concentration of negative and positive ions in the water.

Accordingly, in the locating system of oxidation/reduction potential of the electrolysis water and the constant output method of calibration and compensation thereof of the present invention, when the user drinks the reduction water, the reduction potential of the reduction water can be set in the standard range between −200 mv and −400 mv, and when the user uses the oxidation water, the oxidation potential of the oxidation water can be set in the standard range between +960 mv and +1,200 mv.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A constant output method of calibration and compensation of a locating system of oxidation/reduction potential of an electrolysis water, comprising the steps of:

storing experimental data, coordinate parameters and expressions of an oxidation/reduction potential relative to a plurality of primary factors in a central processing unit to obtain indication values;

detecting actual data of the oxidation/reduction potential of an actual electrolysis water;

comparing and calibrating the indication values with the oxidation/reduction potential of the actual electrolysis water;

selecting an ideal section of the oxidation/reduction potential according to the actual indication values;

performing a step control according to a relative electrolytic current of the ideal section to select the step of the oxidation/reduction potential;

detecting changes of resistance of an electrolytic bath; and regulating a voltage of the electrolytic bath so as to control an electrolytic current of the electrolytic bath exactly, so that the electrolytic current of the electrolytic bath is maintained at a constant value.

2. The method in accordance with claim 1, wherein the primary factors includes the electrolytic time (the flow speed of input water).

3. The method in accordance with claim 1, wherein the primary factors includes the electrolytic current (the current density).

4. The method in accordance with claim 1 wherein the primary factors includes the kinds of electrolyte (the proportion and concentration of negative and positive ions).

5. The method in accordance with claim 1, wherein the actual data of the oxidation/reduction potential is detected by a detection member of the locating system.

6. The method in accordance with claim 5, wherein the detection member includes a shunt resistor mounted in the electrolytic bath, the locating system comprises a main control circuit including a current detection and comparison circuit, a voltage compensation and comparison circuit, a constant current control circuit having a gate driver, and a voltage modulation circuit, and the current detection and comparison circuit and the voltage compensation and comparison circuit can drive the voltage modulation circuit and the gate driver of the constant current control circuit to regulate the voltage, so that the output electrolytic current is kept constant.

7. The method in accordance with claim 5, wherein the detection member includes a flow meter to detect the flow speed of input water in the electrolytic bath, and to transmit the signals of the flow speed of input water to the central processing unit to manually or automatically control the flow rate of the electrolysis water, so as to control the electrolytic time and the flow speed of input water.

8. The method in accordance with claim 5, wherein the detection member includes a TDS test and a PH value test, to detect and transmit data of the total solid quantity and the PH value to the central processing unit for comparison, setting and calibration.

9. The method in accordance with claim 1, wherein the indication values are indicated by a liquid crystal display.

10. The method in accordance with claim 1, wherein the indication values are compared with the oxidation/reduction potential of the electrolysis water by the central processing unit.

11. The method in accordance with claim 1, wherein the resistance of the electrolytic bath is detected by a detection circuit.

12. The method in accordance with claim 1, wherein the voltage is regulated by a voltage modulation circuit.

13. The method in accordance with claim 1, wherein the locating system comprises a manipulation unit including a step selection and an ORE display.

14. The method in accordance with claim 1, wherein the relative electrolytic current of the ideal section can be processed by a stepless control to obtain the relative oxidation/reduction potential.

* * * * *